US009216141B2

(12) United States Patent
Zech et al.

(10) Patent No.: US 9,216,141 B2
(45) Date of Patent: Dec. 22, 2015

(54) CURABLE COMPOSITION, PROCESS OF PRODUCTION AND USE THEREOF

(75) Inventors: Joachim W. Zech, Kaufering (DE); Hendrik Grupp, Inning A. Ammersee/Bachem A. Woerthsee (DE); Thomas Klettke, Diessen (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 40 days.

(21) Appl. No.: 13/819,002

(22) PCT Filed: Aug. 23, 2011

(86) PCT No.: PCT/US2011/048773
§ 371 (c)(1),
(2), (4) Date: Feb. 26, 2013

(87) PCT Pub. No.: WO2012/033633
PCT Pub. Date: Mar. 15, 2012

(65) Prior Publication Data
US 2013/0157226 A1  Jun. 20, 2013

(30) Foreign Application Priority Data
Sep. 9, 2010  (EP) .................................... 10175996

(51) Int. Cl.
*A61K 6/10*   (2006.01)
*A61C 9/00*   (2006.01)
*A61K 6/087*  (2006.01)

(52) U.S. Cl.
CPC ... *A61K 6/10* (2013.01); *A61C 9/00* (2013.01); *A61K 6/087* (2013.01)

(58) Field of Classification Search
CPC ......... A61K 6/10; A61K 6/005; A61K 6/087; A61C 9/00
USPC .......................................... 523/109; 433/214
See application file for complete search history.

(56) References Cited

U.S. PATENT DOCUMENTS

| 3,453,242 A | 7/1969 | Schmitt |
| 3,735,007 A | 5/1973 | Lapidus |
| 3,842,019 A | 10/1974 | Kropp |
| 4,038,113 A | 7/1977 | Oberth |
| 4,122,038 A | 10/1978 | Sandner |
| 4,167,618 A | 9/1979 | Schmitt |
| 4,268,310 A | 5/1981 | Nemeth |
| 4,369,122 A | 1/1983 | Schubart |
| 4,431,421 A | 2/1984 | Kawahara |
| 4,532,268 A | 7/1985 | Jochum |
| 4,600,766 A | 7/1986 | Arita |
| 4,657,959 A | 4/1987 | Bryan |
| 4,691,045 A | 9/1987 | Fukuchi |
| 4,867,790 A | 9/1989 | Jochum |
| 4,891,400 A | 1/1990 | Schwabe |
| 5,015,413 A | 5/1991 | Nagaoka |
| 5,130,348 A | 7/1992 | Zahler |
| 5,234,964 A | 8/1993 | Lin |
| 5,249,862 A | 10/1993 | Herold |
| 5,286,105 A | 2/1994 | Herold |
| 5,419,460 A | 5/1995 | Herold |
| 5,464,131 A | 11/1995 | Keller |
| 5,502,144 A | 3/1996 | Kuo |
| 5,569,691 A | 10/1996 | Guggenberger |
| 5,595,487 A | 1/1997 | Ario |
| 5,656,703 A | 8/1997 | Costin |
| 5,750,589 A | 5/1998 | Zech |
| 5,792,821 A | 8/1998 | Bowen |
| 5,918,772 A | 7/1999 | Keller |
| 5,925,723 A | 7/1999 | Friebe |
| 5,945,466 A | 8/1999 | Ikeno |
| 5,981,740 A | 11/1999 | Bownen |
| 6,057,380 A | 5/2000 | Birbaum |
| 6,075,068 A | 6/2000 | Bissinger |
| 6,084,004 A | 7/2000 | Weinmann |

(Continued)

FOREIGN PATENT DOCUMENTS

| DE | 19753456 | 6/1999 |
| DE | 10058846 | 6/2002 |

(Continued)

OTHER PUBLICATIONS

"Environmental Coatings Glossary" [online]. EnviroTech Financial, Inc., Orange, CA, 2002-2008 [retrieved on Oct. 17, 2008]. Retrieved from the Internet: <URL:http ://www.etfinancial. coml coatingsgloss .htm>; 9 pgs.
Houben Weyl book excerpt, "Methods of Organic Chemistry", Georg Thiene Publishing Company, Stuttgart, 17 (1963).
Jones, "Species in the Polymerization of Ethylenimine and N-Methylethylenimine", Journal of Organic Chemistry, Jun. 1965, vol. 30, No. 6, pp. 1994-2003. [Page number are not legible for this reference. It was already saved in the WS].
Ullmann's Encyclopedia of Industrial Chemistry, 4th Edition, vol. 24, 1983, 3 Pages.
"Zinsser Glossary of Painting Related Terms" [online]. Zinsser Co., Inc., Somerset, NJ, 2003 [retrieved on Oct. 17, 2008]. Retrieved from the Internet :< URL <http://www.zinsser.com/glossary. asp?letter=R>, 3 pgs.
1507 Extended European Search Report for Application No. 10175996.7 dated Mar. 1, 2011, 6 pages.
International Search Report for PCT International Application No. PCT/US2011/048773, Mailed Dec. 23, 2011, 5 pages.

(Continued)

*Primary Examiner* — Tae H Yoon

(57) ABSTRACT

The present disclosure relates to a curable composition to be prepared by mixing a base paste and a catalyst paste, the base paste comprising (A) a hardenable compound comprising at least two aziridine moieties, and (B) a metal containing component containing anions and/or ligands, the metal containing component being present in an amount of about 0.1 to about 5 wt.-%, the metal being selected from Zn, Cu, Co, Ni, Ag and combinations thereof, the anions or ligands being selected from oxide, hydroxyl, (hydro)carbonate, sulphate, nitrate, halide, lactate, benzoate, wolframate, linear or branched aliphatic carboxylic acid anions, ligands having not more than two coordinating moieties and combinations thereof, the catalyst paste comprising (C) a Lewis acid, the composition optionally further comprising (D) a retarder, (E) filler and (F) additive(s). The present disclosure also relates to a kit of parts, the use of a metal containing component and a method of taking a dental impression.

22 Claims, No Drawings

(56) References Cited

U.S. PATENT DOCUMENTS

| | | |
|---|---|---|
| 6,127,449 A | 10/2000 | Bissinger |
| 6,135,631 A | 10/2000 | Keller |
| 6,180,739 B1 | 1/2001 | Bowen |
| 6,218,461 B1 | 4/2001 | Schwabe |
| 6,232,361 B1 | 5/2001 | Laksin |
| 6,244,740 B1 | 6/2001 | Wagner |
| 6,281,307 B1 | 8/2001 | Muhlebach |
| 6,291,546 B1 | 9/2001 | Kamohara |
| 6,383,279 B1 | 5/2002 | Eckhardt |
| 6,395,801 B1 | 5/2002 | Bissinger |
| 6,503,994 B1 | 1/2003 | Nehren |
| 6,541,657 B2 | 4/2003 | Abe |
| 6,583,248 B1 | 6/2003 | Bowen |
| 6,599,960 B1 | 7/2003 | Eckhardt |
| 6,610,759 B1 | 8/2003 | Chappelow |
| 6,686,330 B2 | 2/2004 | Jordan, IV |
| 6,767,980 B2 | 7/2004 | Yurugi |
| 6,794,481 B2 | 9/2004 | Amagai |
| 6,835,785 B2 | 12/2004 | Ishii |
| 6,841,111 B2 | 1/2005 | Rickner |
| 6,855,785 B2 | 2/2005 | Baumgart |
| 6,867,246 B2 | 3/2005 | Nowak |
| 6,894,144 B1 | 5/2005 | Zech |
| 6,906,117 B2 | 6/2005 | Nowak |
| 7,838,572 B2 | 11/2010 | Klettke |
| 8,007,579 B2 * | 8/2011 | Klettke et al. ............... 106/38.2 |
| 8,415,266 B2 | 4/2013 | Eckhardt |
| 2001/0004082 A1 | 6/2001 | Keller |
| 2003/0109596 A1 | 6/2003 | Wanek |
| 2003/0153726 A1 | 8/2003 | Eckhardt |
| 2004/0085854 A1 | 5/2004 | Pauser |
| 2004/0146713 A1 | 7/2004 | Schaub |
| 2004/0149164 A1 | 8/2004 | Eckhardt |
| 2006/0069180 A1 | 3/2006 | Bublewitz |
| 2006/0106127 A1 | 5/2006 | Klettke |
| 2006/0247327 A1 | 11/2006 | Klettke |
| 2007/0090079 A1 | 4/2007 | Keller |
| 2008/0200585 A1 | 8/2008 | Klettke |
| 2009/0047620 A1 | 2/2009 | Klettke |
| 2009/0068619 A1 | 3/2009 | Klettke |

FOREIGN PATENT DOCUMENTS

| | | |
|---|---|---|
| EP | 232733 | 8/1987 |
| EP | 231420 | 9/1991 |
| EP | 863088 | 9/1998 |
| EP | 1277777 | 1/2003 |
| EP | 2266526 | 12/2010 |
| WO | WO 2005-013924 | 2/2005 |
| WO | WO 2005-016783 | 2/2005 |
| WO | WO 2007-047381 | 4/2007 |
| WO | WO 2007-104037 | 9/2007 |
| WO | WO 2009-061884 | 5/2009 |

* cited by examiner

CURABLE COMPOSITION, PROCESS OF PRODUCTION AND USE THEREOF

CROSS REFERENCE TO RELATED APPLICATIONS

This application is a national stage filing under 35 U.S.C. 371 of International Application No. PCT/US2011/048773, filed Aug. 23, 2011, which claims priority to European Application No. 10175996.7 filed Sep. 9, 2010. The disclosures of both applications are incorporated by reference in their entirety herein.

FIELD OF THE INVENTION

The invention relates to a curable composition comprising a transition metal containing salt and a cationically hardenable compound. The composition is particularly useful in various fields or for producing a wide variety of materials including bondings, adhesives, paintings, coatings, printing inks, dental materials, photo resists.

BACKGROUND ART

Dental impression materials are used to record the oral situation of a patient. The resulting hardened impression material captures the negative of the oral situation.

Most dental impression materials are typically delivered in a two or more paste form, containing a base paste and a catalyst paste, which are mixed prior to their application. The mixed pastes are typically applied with the help of a dental tray and/or a syringe-type device. Usually the hardened material can be removed after about one to about six minutes after application. The hardened impression material is used either for making a provisional restoration using a temporary crown and bridge material or for producing a positive model of the oral situation by casting the mould with e.g. gypsum. The obtained positive model is used for making the final restoration in the dental laboratory.

Different types of chemistry can be employed to formulate impression materials. Often used are polyether impression materials which cure by a cationic ring-opening polymerization of aziridines (e.g. Impregum™, 3M ESPE). Aziridine moieties containing components are typically cured by using acids.

Strong acids which can be used include substances like sulfonium salts, especially alkyl sulfonium salts or sulfonium salts derived from glutaconic acid. Those and others are described e.g. in US 2008/0200585 A1 (Klettke et al.), U.S. Pat. No. 4,167,618 (Schmitt et al.) and US 2003/0153726 A1 (Eckhardt et al.).

These materials are acknowledged for their beneficial curing properties which include a comparatively long working time and a so-called "snap-set" curing behaviour. This means, that the viscosity of these materials in the mixed state does not change significantly until the end of the working time and when the working time is over, a rapid curing takes place.

Especially when a long working time is desired, there may be the need to further accelerate the speed of the curing reaction to reduce the time during which a patient is treated with the impression material.

A long working time can e.g. be achieved by using imidazolium compounds as described in EP 0 110 429 A2 (Jochum et al.). The use of these compounds normally does not only increase the working time of the impression material but also increases the curing time in the mouth for the patients and often the curing time is more affected than the working time, unfortunately.

To accelerate the curing of these kinds of materials, the use of sulfonamide compounds is suggested in US 2006/0247327 (Klettke et al.). This document refers to a dental composition comprising ethylene imine compounds and a non-reactive compound containing a $SO_2$—NH group. It is stated that by adding this non-reactive compound the speed of set of the composition to be hardened can be accelerated. Typically, the working time is also reduced. Adding sulphonamide groups containing compounds is, however, not always possible or desirable.

US 2004/0149164 (Eckhardt et al.) relates to a mixture of elongated N-alkylaziridine prepolymers which can be used as a dental material. The mixture can contain various modifiers like finely divided fillers, pigments, thixotropic agents and surface-active substances.

U.S. Pat. No. 6,599,960 (Eckhardt et al.) relates to storage-stable cationically polymerizable preparations with improved hardening characteristics. The preparations can contain 0.0005 to 50 wt.-% of soluble and/or fine-particle organic and/or inorganic alkaline earth and/or alkali metal compounds. The preparation can be used for making dental impressions.

US 2003/0153726 (Eckhardt et al.) relates to a catalyst component containing a Broensted acid, water and at least one antacid-acting compound.

US 2009/0068619 (Klettke et al.) describes a dental composition comprising a prepolymer and a crosslinker having a molecular structure being different from the molecular structure of the prepolymer. The composition can also comprise a filler selected from non-reinforcing fillers and reinforcing fillers.

US 2009/0047620 (Klettke et al.) relates to self-disinfecting plastics, in particular to polyether or silicone based dental plastics and impression materials. The composition can also comprise a filler selected from non-reinforcing fillers and reinforcing fillers.

SUMMARY OF INVENTION

Especially from a practitioner's standpoint of view it would be desirable to have a material at hand, which shows an improved setting behaviour, especially an enhanced speed of set, ideally—but not mandatory—combined with sufficient elastic properties.

In one embodiment, the invention features a curable composition to be prepared by mixing a base paste and a catalyst paste, the base paste comprising
(A) a hardenable compound comprising at least two aziridine moieties, and
(B) a metal containing component containing anions and/or ligands,
  the metal containing component being present in an amount of about 0.1 to about 10 wt.-% or about 0.2 to about 5 wt.-% with respect to the weight of the base paste,
  the metal being selected from Zn, Cu, Co, Ni, Ag and combinations thereof,
  the anions or ligands being selected from oxide, hydroxyl, (hydrogen)carbonate, (hydrogen)sulphate, (hydrogen)phosphate, nitrate, halide, lactate, benzoate, wolframate, linear or branched aliphatic carboxylic acid anions, ligands having not more than two coordinating moieties and combinations thereof, (E) filler being different from the metal containing component, the catalyst paste comprising (C) a Lewis acid, the composition optionally further comprising (D) a retarder, and (F) additive(s).

In another embodiment, the invention features a process of producing such a composition comprising a mixing step.

The invention is also directed to a kit of parts comprising a base paste and a catalyst paste, the base paste comprising a hardenable compound comprising at least two aziridine moieties and a metal containing component in an amount of about 0.1 to about 5 wt.-%, the transition metal being selected from Zn, Cu, Co, Ni, Ag and mixtures thereof, the catalyst paste comprising a Lewis acid, the catalyst paste being essentially free of the metal containing component being present in the base paste.

A further embodiment of the invention is directed to the use of the composition as described in the text of the invention as or for producing dental material(s).

A further embodiment of the invention is directed to the use of the metal containing component as described the present text as a means for reducing the curing time of a cationically curable composition.

Moreover, the invention features a method of taking an impression of dental tissue, comprising the steps of a) applying the curable composition to the surface of dental tissue, b) letting the curable composition set, c) removing the set composition from the dental tissue.

It has been found that the composition described in the text of the invention fulfils the practitioners' needs especially with regard to properties like setting or curing behaviour.

Surprisingly it has been found that the curing behaviour of the curable composition can be modified by adding comparable small amount of metal containing components.

It has also been observed that by using small amounts of certain metal containing components the curing time can be shortened.

With respect of certain embodiments it has also been observed that the cured compositions are still sufficiently elastic and show e.g. good elongation at break properties.

Moreover, the composition can be cured by ambient conditions, including room temperature (e.g. between about 15 to 25° C.).

The surface of certain compositions is typically tack free after curing.

Certain embodiments of the inventive composition may also have a sufficient shelf life, that is, they can be stored for a sufficient period of time without negatively affecting the desired properties.

Depending on the chosen backbone of the prepolymer bearing the aziridino group(s), the inventive composition can be highly hydrophilic.

Within the description of the invention, the following terms are defined as follows:

The term "compound" is a chemical substance which has a particular molecular identity or is made of a mixture of such substances, e.g., polymeric substances.

By "paste" is meant a soft, viscous mass of solids dispersed in at least one liquid or a soft, viscous mass of a polymer.

A "hardenable compound" is any compound which can be cured or solidified e.g. by chemical crosslinking. Chemical crosslinking can be initiated by using a redox or ionic initiator, radiation or heating thereby typically leading to a significant change in rheological properties like viscosity.

A "starter or initiator" is a substance or a group of substances being able to start or initiate the hardening process of a hardenable compound.

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

The term "cationically polymerizable compound" is defined as a compound which can be polymerised using an initiator containing or being able to generate cations, especially reactive cations.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group which is a three membered heterocycle with one amine group and two methylene groups. The parent compound of the aziridines is called aziridine with molecular formula $C_2H_5N$. The curing of aziridines can be effected by a cationically curing mechanism using strong acids e.g. Lewis acids.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group. In the chemical literature a "methyl substituted aziridine" is sometimes also referred to as "propylene imine".

"Polyether" or "polyether group containing compound" are compounds having a molecular weight of at least about 150 g/mol and containing in the backbone at least about 3, 10 or 20 ether moieties. Polyether containing compositions used as dental impression material can be cured by different mechanisms. Widely used is a crosslinking reaction using aziridine groups.

Examples of polyether groups containing impression materials are given in U.S. Pat. No. 5,569,691 (Guggenberger et al.), US 2004/0146713 A1 (Schaub et al.) and US 2006/0069180 (Bublewitz et al.) Commercially available materials are sold e.g. under the brand Impregum™ (3M ESPE).

By "derivative" is meant a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition.

A "particle" means a substance being a solid having a shape which can be geometrically determined. The shape can be regular or irregular. Particles can typically be analysed with respect to e.g. grain size and grain size distribution. Fillers typically comprise, essentially consist of or consist of particles.

"Room temperature curable" implies that the curing reaction can proceed at temperatures at or near about 15 to 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

By "dental composition" is meant a composition which is intended and adapted to be used in the dental field (including restorative and prosthodontic work) including the orthodontic area. In this respect, a dental composition typically does not contain hazardous substances. Commercially available products have to fulfil requirements such as those given in ISO 4823. Typically, those compositions cure or set at ambient conditions.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva. Common materials used for dental impressions include alginate, agar, polyethers including aziridine substituted polyether materials as well as silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE AG under the trademarks Reprogum™ or Vestogum™.

The term "automixer-suitable impression material" relates to a multi-component impression material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (see also U.S. Pat. Nos. 5,286,105 and 5,249,862).

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Krüss). A low water contact angle indicates a better wettability.

"Molecular weight" in the context of the invention and if not otherwise indicated always means number average molecular weight ($M_n$). The molecular weight ($M_n$) of the polymerizable compound before setting can be determined using nuclear magnetic resonance spectroscopy (end-group determination). In this respect proton ($^1H$) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may for example be a pressure of about 900 to about 1100 mbar. a temperature of about −10 to about 60° C. and a relative humidity of about 10 to about 100%. In the laboratory ambient conditions are adjusted to about 23° C., about 1013 mbar and about 50% rel. humidity.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all.

However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4.5, etc.).

Unless otherwise indicated, all numbers expressing quantities of ingredients, measurement of properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention.

Certain embodiments of the curable composition can be characterized by at least one or more of the following features:

Consistency (according to ISO 4823): 0, 1, 2 or 3,
Setting time: within about 15 min after mixing at ambient conditions (e.g. 23° C.), That is, the hardenable composition (that is, in its uncured state) can show a comparable low viscous behaviour (consistency 3), a medium to high viscosity (consistency 1 or 2) or show a putty-like behaviour (consistency 0).

Certain embodiments of the hardened composition can be characterized by at least one or more of the following features:

Tensile strength (according to DIN 53504): at least about 0.2 MPa, or at least about 1.0,
Elongation at break (according to DIN 53504): at least about 30%, or at least about 50%, or at least about 100%,
Recovery from deformation (according to ISO 4823): at least about 90%, or at least about 95%, or at least about 98%,
Shore A hardness (according to DIN 53505; 24 h): equal to or above about 20 or 30 or 40, wherein a range from about 40 to about 70 can be preferred.
Elastic deformation (according to ISO 4823): from about 0.2 to about 20% or from about 0.5 to about 10%.

If desired, the viscosity can be measured at 23° C. using a Physica/Anton Paar (MCR 300 or MCR 301) device with a plate/plate system (diameter 20 mm) and a slit of 0.2 mm. The viscosity values (Pas) and share stress values (Pa) are recorded for each share rate (. starting from 10 1/s to 100 1/s in 10 1/s and/or 5 1/s steps. For each share rate, a delay of 5 s is used before collecting data. The above mentioned method of measurement corresponds essentially to DIN 53018-1.

If desired, the tensile strength and elongation at break of the compositions can be determined according to DIN 53504. The tensile strength is given in MPa and the elongation in % of the original length. Tensile strength and elongation data are evaluated by tearing six I-shaped specimens with a central unit of 20 mm×4 mm×2 mm in a Zwick Z020 Universal testing machine. Base and catalyst pastes can be mixed through a static mixer (e.g. SulzerMixpac Comp.), by an automatic mixing device (e.g. Pentamix™; 3M ESPE) or by hand and filled into a brass mould. After 24 h at about 23° C. the specimen are removed, six measurements are made and the mean value determined (speed 200 mm/min).

The hardenable compound typically comprises a backbone and at least two reactive functional groups.

The backbone of the hardenable compound typically comprises moieties selected from polyether, polyester, polyurethane, silicone, polyalkylene, polystyrol, polysulfide and combinations thereof.

In the dental field a polyether moieties containing backbone can be preferred. Those groups typically improve the hydrophilic properties of the composition.

According to one embodiment, the hardenable compound includes a polyether group containing hardenable prepolymer as component (A) or part of component (A), that is, a prepolymer comprising a polyether group(s) and reactive moieties which upon addition of a suitable catalyst or initiator can react with each other and thus form a polymeric network.

The molecular weight ($M_n$) of the polyether group(s) containing prepolymer is typically in a range from about 150 to about 20,000 g/mol, or in the range from about 250 to about 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The hardenable compound comprises on average at least 2 aziridine moieties or more, if desired, e.g. at least 3 or 4 or 5 or 6.

The term "on average" is to be interpreted such in the context of the present text that a mixture of a large number of compounds may comprise both compounds having less than 2 aziridino groups and also compounds having more than 2 aziridino groups although, when seen over the entirety of the compounds of component (A), the average functionality of all molecules is, with respect to aziridino groups, 2 or more.

Suitable possible methods for providing the polymers with aziridino groups are mentioned, e.g., in U.S. Pat. No. 3,453, 242 (Schmitt et al.).

Suitable polymers carry the aziridino groups terminally or laterally, or terminally and laterally, but preferably terminally.

As the curing reaction of aziridino moieties is typically effected by a cationically curing mechanism, the hardenable compound can also be characterized as a cationically curing compound.

The aziridino groups containing polymers typically have a dynamic viscosity $\eta$ of from 10 to about 500 Pa*s, especially from about 15 to about 300 Pa*s. A preferred viscosity range is from about 20 to about 180 Pa*s at 23° C.

The aziridino equivalent is typically from about 250 to about 25,000 g/equivalent, especially from about 400 to about 10,000 g/equivalent. The term "aziridino equivalent" is defined as (molecular mass of the molecule)/(number of aziridino groups present in the molecule).

The hardenable compound which can be used may comprise only one type of aziridino group containing polymer. It is, however likewise possible for the cationically hardenable compound to comprise two or more different types of aziridino polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups pending from or attached to the backbone of the prepolymer include those characterized by the following formula (I)

$$—(L)_x—G—E—N{\overset{R}{\diagup}}\!\!\triangleleft \qquad (I)$$

wherein

R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S, E represents a C1-C18 branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)(CH2)mC(O) with m=1 to 10, C(S)NR, CH2, L represents O, S, NR with x=0 or 1.

It can be preferred, if the prepolymer has a linear molecular structure. Thus, the prepolymer may typically comprise a linear backbone, which is typically end-capped with cationically hardenable moieties, including aziridino groups. Usually, there are no side chains, especially cationically hardenable side chains pending from the backbone.

The hardenable compound is typically present in an amount of at least about 5 wt.-% or at least about 12 wt.-% or at least about 20 wt.-%.

The hardenable compound is typically present up to an amount of about 95 wt.-% or up to about 80 wt.-% or up to about 75 wt.-%.

Typical ranges include from about 5 wt.-% to about 90 wt.-% or from about 12 wt.-% to about 80 wt.-% from about 25 wt.-% to about 70 wt.-%.

The hardenable compound is typically present in an amount, which allows the formation of a sufficiently crosslinked network, in order to fulfil the practitioners needs.

By varying the amount of the hardenable compound, e.g. the viscosity and the hardness of the cured composition can be adjusted.

If the amount of the hardenable compound is too low, the resulting composition might not cure within the desirable period of time or might show not desirable mechanical properties.

If the amount of the hardenable compound is too high, the resulting composition might be too viscous.

If desired, besides the curable compound containing at least two aziridino groups, further curable compounds can be present being different from the cationically hardenable compound described above.

Thus, blends of various polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000).

The curable composition contains as an initiator a Lewis acid. The initiator is present in the catalyst paste.

Useful initiators for starting, initiating or participating in the curing reaction include:

Initiator substances which make possible curing of the mixed preparation at ambient conditions in a period of from about 1 to about 20 min to form a resilient solid body, that solid body meeting the requirements for a resilient impression material according to DIN/EN 4823 and having a Shore A hardness (DIN 53 505) of at least 20 after 24 hours.

Sulfonium salts, especially alkyl sulfonium salts or sulfonium salts derived from glutaconic acid were found to be useful. Those and others are described e.g. in US 2008/0200585 A1 (Klettke et al.), U.S. Pat. No. 4,167,618 (Schmitt et al.) and US 2003/0153726 A1 (Eckhardt et al.), the content of which in regard to initiators is explicitly mentioned and herewith incorporated by reference.

E.g. trialkylsulfonium salts as are described in, for example, U.S. Pat. No. 4,167,618 (Schmitt et al.) (e.g.: column 2, line 36—column 4, line 32 and Examples) are suitable as initiator substances. The mentioned trialkylsulfonium salts are understood as being part of the disclosure of the present text.

Particular examples of suitable initiators include: S-lauryl-S-ethylsulfonium)butyronitrile tetrafluoroborate, dodecylbenzenesulfonic acid zinc salt, (S-lauryl-S-ethylsulfonium)-phenylacrylic acid butyl ester tetrafluoroborate.

A further preferred class of initiators can be classified as sulfonium salts or derivatives of glutaconic acid esters as describe in US 2008/0200585 A1 (Klettke et al.). The content of this application with respect to the description of initiators and the way how they can be produced is especially mentioned and herewith incorporated by reference and regarded as part of this invention.

The term "glutaconate" within the meaning of the invention comprise the free glutaconic acid, the partly or de-protonated form of the glutaconic acid (salt of the acid) or an ester (mono-or di-ester) thereof or combinations of gluta-conic acid, partly or de-protonated species or esters.

These initiators comprise at least one structural element of the following formula (II)

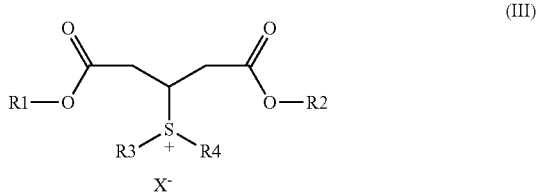

(III)

wherein
X– is a non or low coordinating anion,
R1, R2, R3 and R4 are independently linear, cyclic or branched C1-C20 alkyl or alkylene groups, wherein one or more of the methylene groups may be substituted by —CO—, —CONH—, —CON(CH3)-, —S— and/or —O—,
and wherein R1, R2, R3 and/or R4 can act as a bridging element, connecting two or more structural elements.

Subject to the question whether bridging elements are present or not, the initiator can be characterized as monomer, dimer, trimer, higher oligomer or polymer with one, two, three, four or more sulfonium groups.

The term "non or low coordinating group" within the meaning of the invention are anions of strong acids, preferably acids having a pKs value below about 2. Respective examples are $BF_4^-$, $CF_3SO_3^-$, $SbF_6^-$, $AsF_6^-$ or 2,5-di-chloro-benzolsulfonate, but even other low coordinating anions can be used.

The term "bridging element" within the meaning of the invention is defined as a chemical group being able to connect two or more of the aforementioned structural elements comprising at least one sulfonium group. Examples of bridging elements include —(CH$_2$)$_8$—, —(CH$_2$)$_6$— or —(CH$_2$)$_4$— moieties.

Particular examples of initiators which can be used include also those described in US 2008/0200585 (Klettke et al.) from section [0040] to section [0064].

The molar ratio between the initiator and the hardenable compound includes ranges from about 1.0:0.1 to about 1.0:20.0, or from about 1.0:0.5 to about 1.0:10.0, or from about 1.0:0.8 to about 1.0:30.

As the initiator does not only act as a catalyst but chemically react—to a certain extend—with the hardenable composition, a sufficient amount of initiator should be present.

The amount of initator to be used is not particularly limited, unless the desired curing reaction cannot be initiated or catalyzed.

The initiator is typically present in an amount of at least about 0.1 wt.-% or at least about 0.5 wt.-%.

The initiator is typically present up to an amount of about 50 or up to about 35 wt.-% or up to about 20 wt.-%.

Typical ranges for the initiator include from about 1 wt.-% to about 50 wt.-% or from about 3 wt.-% to about 40 wt.-% from about 4 wt.-% to about 25 wt.-%, wt.-% with respect to the weight of the whole composition.

The inventive composition comprises a metal containing component. The metal containing component is typically present in the base paste of the composition.

The metal containing component is typically used in a comparable small amount and is not regarded as a filler. Typical fillers do usually not interact with the kinetic of a curing reaction.

The metal being contained in the metal containing component is selected from Zn, Cu, Co, Ag, Ni and mixtures or combinations thereof. The metal is typically present as a cation.

The metal containing component can be a salt or a complex. Thus, the component comprises not only the metal or the metal cation but also an anion and/or one or more ligands (sometimes also referred to as complexing agent)

Ligands are generally bound to a metal ion by a coordinative bonding (donating electrons from a lone electron pair to the Lewis acidic metal centre), and are thus said to be coordinated to the ion.

Typical anions include oxide, hydroxyl, (hydrogen)carbonate, hydroxycarbonate, sulphate, phosphate, halide (e.g. chloride and bromide), lactate, benzoate, wolframate, linear or branched aliphatic carboxylic acid anions (e.g. C2 to C18) and combinations thereof. Particular examples of the carboxylic acid anions include stearate, decanoate, ethylhexanoate and palmitate.

Suitable anions typically have a pKs value greater than about 7. That is, in aqueous environment the anions do not behave as acids but rather neutral or basic.

Typically ligands include those which do not have more than two coordinating moieties.

Examples include acetyl acetonate, gluconate, gluturate, salicylate, glycinate, lactate, propylendiamine and ascorbate, combinations and mixtures thereof.

The metal containing component is typically present in the base paste only.

Without wishing to be bound to a certain theory, it is believed that the metal—once released from the metal containing compound—is somehow interacting with the amino functions generated upon ring-opening of the aziridino moieties. Maybe a certain kind of complex is formed between the amino groups being present in the crosslinkable prepolymer and the metal (ion). Thus, the metal (ion) might help to coordinate the reactive groups and facilitate the crosslinking reaction between those groups.

Metal containing components having a certain solubility in the surrounding components were found to be useful. Hardly soluble metal containing compounds like hardly soluble salts (e.g. ZnS) are typically not suitable. Also metal complexes having high coordinating ligands (e.g. ligands having more than 3 or 4 coordinating moieties) are typically not suitable.

Specific examples of metal containing components which can be used include: zinc oxide, zinc hydroxide, zinc carbonate, zinc hydroxyl carbonate, zinc wolframate, zinc acetylacetonate, zinc bis(neodecanoate), zinc stearate, copper sulphate, copper 2-ethylhexanoate, nickel acetlyacetonate, silver carbonate, mixtures and combinations thereof.

Typically, only small amounts of metal containing compound are needed.

Amounts from about 0.1 to about 10 wt.-% or from about 0.2 to about 5 wt.-% or from about 0.5 to about 3 wt.-% with respect to the weight of the base paste are typically sufficient.

The molar ratio of metal containing component to initiator is typically from 10 to 1 to 1 to 10 or from 5 to 1 to 1 to 5 or from about 2 to 1 to 1 to 2.

The molar ratio of metal containing component to the aziridino moieties being present in the curable compound is typically from 10 to 1 to 1 to 10 or from 5 to 1 to 1 to 5 or from about 2 to 1 to 1 to 2.

If the ratio is below those values, the desired acceleration of the curing time might be difficult to achieve. If the ratio is above those values, the storage stability or shelf life might be negatively affected. E.g. if the amount of metal containing component used is too high, the hardening reaction might occur too fast. If on the other hand the amount of metal containing component is too low, the storage stability might be not sufficient.

According to a further embodiment the composition can also comprise one or more retarders.

Suitable retarders include those which comprise an imidazole moietiy.

In principle, imidazole itself and all 1-substituted imidazole derivatives are suited for the purpose of the invention, provided they are soluble in the particular aziridine compound(s) employed. Imidazoles more sparingly soluble in the aziridine compounds employed may be dissolved by the addition of plasticizers such as phthalic acid esters, as solubilizers. Preferably, 1-substituted imidazoles are employed For example, the imidazoles may have the general formula C3H3N2-R, wherein R represents: C1-C18 alkyl, substituted C1-C18 alkyl, C3-C12 cycloalkyl, substituted C3-C12 cycloalkyl, C2-C18 alkenyl, substituted C2-C18 alkenyl, substituted phenyl or H.

Examples of suitable imidazole compounds include 1-methylimidazole, 1-(n-butyl)imidazole, 1-decylimidazole, 1-laurylimidazole, 1,.omega.-bis(1-imidazolyl)-C1-C10 alkanes such as 1,2-bis(1-imidazolyl)ethane and 1,10-bis(1-imidazolyl)decane, 11-(1-imidazolyl)undecanoic acid benzylamide, 1-cyclohexylimidazole, 1-benzylimidazole, 1-(2-ethoxyethyl)imidazole, 1-(4-methoxyphenyl)imidazole, and 1-[3-(2-ethylhexanoyl)amidopropyl]-imidazole.

This kind of retarder is also described in U.S. Pat. No. 4,532,268 (Jochum et al.).

If present, the retarder is typically present in an amount of at least about 0.1 wt.-% or at least about 0.5 wt.-%.

The retarder is typically present up to an amount of about 10 or up to about 5 wt.-% or up to about 2 wt.-%.

Typical ranges for the initiator include from about 0.1 wt.-% to about 10 wt.-% or from about 0.2 wt.-% to about 5 wt.-% from about 0.5 wt.-% to about 2 wt.-%, wt.-% with respect to the weight of the whole composition.

The curable composition may comprise a filler or filler matrix. The filler matrix can be comprised of one filler or a mixture of different fillers.

The nature of filler is not particularly limited. The size of the filler particles should be such that a homogeneous mixture with the hardenable component(s) forming the resin matrix can be obtained.

The BET surface of the filler is typically in a range from about 0.05 to about 50 m$^2$/g or from about 0.5 to about 30 m$^2$/g or from about 0.5 to about 20 m$^2$/g. Using a filler with a BET surface within this range can be beneficial to adjust the viscosity and tensile strength.

If desired, the BET surface of the filler can be determined as described in DIN 66132. Alternatively, the values for the BET surface are taken from a material data sheet provided by the supplier.

The size of the filler particles should be such that a homogeneous mixture can be obtained. The particle distribution is preferably chosen such that there are no fillers with particle sizes of more than 200 μm.

Typically, the size of the filler particles (d50 value) is below about 40 μm or below about 10 μm or below about 5 μm. Typical ranges (d50 value) include from about 0.1 to about 40 μm or from about 0.5 to about 20 μm or from about 1 to about 10 μm.

The mean particle size, if desired, can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

If the filler particles are too small, the viscosity of the resulting composition might increase to a not desirable limit.

If the filler particles are too big, the detail accuracy might be negatively affected.

The filler comprises typically a filler body and a filler surface. The filler is typically in particle form.

The filler body typically comprises, consists essentially of or consists of SiO$_2$ moieties. Typical examples include quartz, cristobalite and silicates (e.g. components comprising anions of the formula [SiO$_3^{2-}$]$_n$ or [Si$_2$O$_5^{2-}$]$_n$) like wollastonite, nephelinsyenite, kaolin, talcum, feldspar, and mixtures and combinations thereof, wherein quartz and cristobalite are sometimes preferred.

The surface of this filler may comprise side groups with polar moieties.

By "side group" it is meant that the polar moiety is not directly attached to the filler body (e.g. like Si—OH moieties being present on the surface of a quartz filler), but that the polar moiety is linked to the surface of the filler body by a spacer group.

"Polar moieties" are defined as chemical groups having a dipole moment. Examples of such chemical groups include ethers, alcohols, thiols, phosphines, amines (prim., sec., tert.), amide, urethanes, esters, oxiranes, oxetanes, hydrated furanes, thiiranes and combinations thereof.

Side groups with polar moieties can be attached to the filler surface by applying the following steps: dispersing the filler in a solvent, adjustment of the pH, adding of a silane coupling agent, heat treatment, removal of solvent, drying of the filler, solvent exchange process, milling of the filler.

Silane coupling agents, which can be used for the surface-treatment of the filler include substances which can be characterized by formula (III):

$$E\text{-}F\text{-}G \qquad\qquad (III)$$

wherein E comprises a polar moiety (as described above), F comprises Si, and G comprises at least one hydrolysable group.

By "hydrolysable group" is meant a group, which can react e.g. with OH-groups being present on the surface of the filler.

Examples of hydrolysable groups include halogens (e.g. F, Cl and Br), pseudo-halogens (e.g. azides) and alcoholates (e.g. C1-C6, alkyl and aryl).

More specifically, silane coupling agent which can be used include those which can be characterized by formula (IV)

$$A_m\text{-}B\text{—}Si(R^1)_n(OR^2)_{3-n} \qquad\qquad (IV)$$

with A comprising a polar moiety (including —O—, —S—, —NH—, —OH, —SH, —CO—, —CO—O—, —CO—NH— and combinations thereof, wherein moieties comprising amines, oxiranes, and combinations thereof are preferred, B comprising a spacer group, such as (i) linear or branched C1 to C12 alkyl, (ii) C6 to C12 aryl, (iii) organic group having 2 to 20 carbon atoms bonded to one another by one or more ether, thioether, ester, thioester, thiocarbonyl, amide, urethane, carbonyl and/or sulfonyl linkages, R$^1$ comprising an alkyl group (e.g. C1 to C6) or an aryl group (e.g. C6 to C12), and R$^2$ comprising an alkyl group (e.g. C1 to C6), with m=1, 2, 3 or 4 and n=0, 1 or 2.

Non-polar moieties are e.g. —Si—OR, —Si—O—Si—, —Si—R, with R being alkyl (e.g. C1 to C6) or aryl (e.g. C1 to C6). These kinds of moieties do not show a sufficient dipole moment.

Preferably, the surface of the filler should not contain or be essentially free of acidic groups like —COOH and —SO$_3$H.

The pH value of a 10 wt.-% dispersion of the filler in water is typically within the range from about 6 to about 12. Using a filler having a pH value within this range can be beneficial to improve the storage stability and shelf life of the composition.

The pH value can be determined with means known to the person skilled in the art.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen) and quartz comprising trimethyl-silane groups (e.g. Silbond™ 800 RST).

Besides surface-treated fillers, non-surface treated fillers can be added. A "non-surface treated filler" in the context of the invention is a filler having a surface which has not been exposed to reactive substances resulting in a modification of the surface of the filler to make the filler more compatible with other components of the composition.

A wide variety of inorganic, hydrophilic or hydrophobic fillers may be employed such as silicas, aluminas, magnesias, titanias, inorganic salts, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Cabot Corporation, Wacker or Degussa under the trade names Aerosil™ (Degussa) HDK-H, HDK 2050 (Wacker), Cab-o-Sil (Cabot), Celatom MW25 (Chemag).

More specifically, fillers which can be used include calcium silicate, diatomaceous earth, zirconium silicate, montmorillonite such as bentonite, zeolite, including molecular sieves such as sodium aluminium silicate, barium sulphate, calcium carbonate, plaster, glass and plastic powder.

A combination of a zinc containing compound and a non-reinforcing filler e.g. fillers selected from quartz, diatomaceous earth, quartz, alumina, magnesia and mixtures thereof, was found to be beneficial for providing a curable composition with well balanced properties.

The sizes and surface areas of the foregoing materials can be adjusted to control the viscosity and thixotropicity of the resulting compositions.

A combination of reinforcing and non-reinforcing fillers sometimes even further improves the rheology of the un-cured composition and the elasticity of the cured composition.

Typical reinforcing fillers include fumed silica, carbon black and the like. They also can improve mechanical properties like tensile strength or tear strength, of the cured silicone composition.

Typical non-reinforcing fillers include precipitated silica, diatomaceous earth, alumina, magnesia, titanium dioxide, zirconium silicate and mixtures and combinations thereof.

If a filler is present, the filler is present in an amount of at least about 1 wt.-% or at least about 5 wt.-% or at least about 10 wt.-% with respect to the whole composition.

There is no particular upper limit, however, typically the amount of filler, if present at all, is used in an amount of at most about 80 wt.-% or at most about 75 wt.-% or at most about 70 wt.-% with respect to the whole composition.

Thus, typical ranges for the filler include from about 10 to about 80 or from about 15 to about 75 or from about 20 to about 70 wt.-% with respect to the whole composition.

If the amount of the filler is too low, a desired Shore hardness might not be obtained.

If the amount of the filler is too high, the elasticity of the cured composition might negatively be affected and the viscosity of the un-cured composition might be too high. Moreover, the shelf life might negatively be influenced.

According to a further embodiment the composition can also comprise one or more additives such as accelerators, stabilizers, pigments, dyes, viscosity modifiers, surfactants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER.

Preferred are those ingredients and additives that do not add unpleasant smell or taste. Compounds that have an unpleasant smell might be removed by thinfilm evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene sulfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polytetrahydrofuranes, polyolefines can be used. Also low molecular weight alcohols that may contain more than one OH-function like propane-1,2, diol or carbonates like propylene carbonate may be used. From the group of polymeric compounds, polypropylene glycols and its derivatives are preferred.

An example of a preferred plasticiser combination is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801 (Bissinger et al.), to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, Illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are known to the person skilled in the art. Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in public literature and are known to the person skilled in the art.

Preferred triacyl glycerides correspond to the formula (V):

$$R2-O-CH_2-CH(OR1)-CH_2-O-R3 \quad (V)$$

in which R1, R2 and R3 denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

Suitable thixotropic agent(s) which can be added to the composition of the invention are organic compounds, e.g. waxes according to the definition in Ullmanns Enzyklopädie der technischen Chemie, 4. Auflage, Verlag Chemie, Weinheim, Band 24, page 3 or triglycerides as described in U.S. Pat. No. 6,127,449 (Bissinger et al.). In general all organic non-water based thixotropic agents are suitable. That means that suitable thixotropic agents can alter the rheology especially of non-water based formulation.

The curable composition may also include one or more surfactant(s), especially Si-containing surfactant(s) or mixture of Si-containing surfactants.

If surfactant(s) are present they are typically present in an amount sufficient and not detrimental to the desired effect or effects to be achieved.

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Surfactant(s) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state).

In certain embodiments, the surfactant does not contain reactive groups so that it is not incorporated into the network of the hardenable composition.

Useful surfactants also include polyether carbosilanes of the general formula (VI)

$$Q-P-(OC_nH_{2n})_x-OZ \quad (VI)$$

in which Q stands for $R_3Si-$ or $R_3Si-(R'-SiR_2)_a-R'-SiR''_2-$, where every R in the molecule can be the same or different and stands for an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or $R_3SiR'$ in the case of a=0, and a=0-2; P stands for a C2-C18 alkylene group, preferably a C2-C14 alkylene group or A-R''', where A represents a C2-C18 alkylene group and R''' a functional group selected from: —NHC(O)—, —NHC(O)—$(CH_2)_{n-1}$—, —NHC(O)C(O)—, —NHC(O)$(CH_2)_vC(O)$—, —OC(O)—, —OC(O)—$(CH_2)_{n-1}$—, —OC(O)C(O)—, —OC(O)$(CH_2)_vC(O)$—, —OCH$_2$CH(OH)CH$_2$OC(O)$(CH_2)_{n-1}$—, —OCH$_2$CH(OH)CH$_2$OC(O)$(CH_2)_vC(O)$— with v=1-12; Z is H or stands for a C1-C4 alkyl radical or a C1-C4 acyl radical; x stands for a number from 1 to 200 and n stands for an average number from 1 to 6, preferably 1 to 4. Thus, the element —SiR"$_2$-can also comprise the substructure —Si(R)(R$_3$SiR')—.

Other surfactants which can be used, either alone or as a mixture of two or more thereof, can be found in U.S. Pat. No. 4,657,959 (Bryan et al.), col. 4, I. 46 to col. 6. I. 52 as well as in EP 0 231 420 B1 (Gribi et al.; also published as AU 6,857,087) p4, I. 1 to p. 5, I. 16 and in the examples.

U.S. Pat. No. 5,750,589 (Zech et al.), U.S. Pat. No. 4,657, 959 and EP 0 231 420 B1 are expressly described and cited herein as a source of disclosure for compounds which can be used as component (E1) according to the invention.

Some of the surfactants, which can be used as component (E1) or part of component (E1) can be summarized under the following formula (VII)

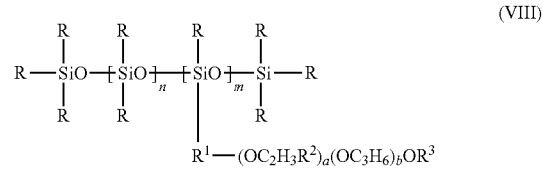

(VIII)

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL™ SF19, as obtainable from Lubrizol performance products, Spartanburg, U.S.

Examples of useful non-ionic surfactants include those according to the formula (VIII):

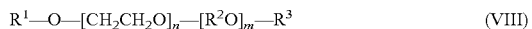

$$R^1\text{—O—}[CH_2CH_2O]_n\text{—}[R^2O]_m\text{—}R^3 \qquad (VIII)$$

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL™X080 from Clariant GmbH.

Non-ionic surfactants according to the above formula with $R^1$ and $R^3$ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

The inventive composition may also comprise in addition to other ingredients and surfactants, alone or in combination an F-containing component including those described in EP application number 09162681.2, especially those described on pages 21 to 27 of this application.

Generally, these substances can be desribed as $(G^1\text{-}L^1\text{-}O)_s\text{—}R_f^a\text{—}O\text{-}L^2\text{-}G^2$ wherein:

$G^1$ and $G^2$ each independently represents a non-ionic end-group that is free of polyoxyalkylene groups or contains polyoxyalkylene such that the total amount thereof in this compound is not more than 10% by weight based on the molecular weight of the compound; $L^1$ and $L^2$ each independently represents an aliphatic hydrocarbon group or a partially or fully fluorinated aliphatic hydrocarbon group; $R_f^a$ represents a mono-valent or divalent partially or fully fluorinated aliphatic group or a partially or fully fluorinated aliphatic group interrupted by one or more oxygen atoms; with the proviso that at least one of the following conditions is fulfilled: (i) at least one of the moieties $L^1\text{-}G^1$ and $L^2\text{-}G^2$ is partially or fully fluorinated or (ii) $R_f$ is a partially or fully fluorinated aliphatic group interrupted by one or more oxygen atoms. The substance HFPO ($C_3F_7O[CF(CF_3)CF_2O]_nCF(CF_3)COOCH_3$ with n being 1 to 8) can be preferred.

There is no need for additive(s) to be present, however, if additive(s) are present, they are typically present in an amount of at least about 0 wt.-% or at least about 0.005 wt.-% or at least about 0.01 wt.-%.

Additives can be present up to an amount of about 50 wt.-% or up to about 40 wt.-% or up to about 35 wt.-%.

Typical ranges include from about 0 wt.-% to about 50 wt.-% or from about 0.005 wt.-% to about 40 wt.-% from about 0.01 wt.-% to about 35 wt.-%.

If additive(s) are present they are typically present in an amount sufficient and not detrimental to the desired effect or effects to be achieved.

The cationically hardenable composition can comprise the individual components in the following amounts:
  (A) hardenable compound comprising at least two aziridine moieties: from about 5 to about 90 wt.-% or from about 10 to about 80 wt.-% or from about 20 to about 70 wt.-%,
  (B) Initiator: from about 0.25 to about 50 wt.-% or from about 0.5 to about 40 wt.-% or from about 1 to about 25 wt.-%,
  (C) metal containing compound: from about 0.1 to about 4 wt.-% or from about 0.2 to about 3 wt.-% or from about 0.5 to about 2.5 wt.-%,
  (D) retarder: from about 0 to about 20 wt.-% or from about 0.1 to about 10 wt.-% or from about 0.5 to about 5 wt.-%,
  (E) filler: from about 1 to about 80 wt.-% or from about 10 to about 75 wt.-% or from about 15 to about 70 wt.-%,
  (F) additive(s) or adjuvant(s): from about 0 to about 50 wt.-% or from about 0.005 to about 40 wt.-% or from about 0.01 to about 35 wt.-%.
wt.-% with respect to the whole composition.

The values given above for the whole composition typically differ from the values given for either the base paste or the catalyst paste.

The composition does typically not contain water, especially added water. However, small amounts of water (e.g. below about 3 wt.-% or below about 1 wt.-%) might be present due to the natural water content of the individual components of the formulation.

If the composition is to be used in the medical or dental field, the composition does typically not contain components which are not desirable form a toxicological standpoint of view and may easily leak from or migrate out of the mixed composition, especially when the composition is placed into a patients' mouth.

According to another embodiment, the composition does not comprise components which can be classified as Broensted acids in an amount above about 1 wt.-% or above about 0.1 wt.-% with respect to the whole composition. It can be desirable not to wilfully add a Broensted acid like those described in US 2003/0153726, classified in this reference as component (A). In particular sulfonic acids, phosphonic acids or carboxylic acids are typically not added or present in the an amount as outlined above.

According to a further embodiment Broensted acids are especially not contained in the catalyst paste in an amount above about 1 or above about 0.1 wt.-%.

The invention is also directed to a process of production or manufacturing the composition.

Such a process typically comprises at least one mixing or compounding step of the individual component of the composition. Mixing or compounding can be accomplished by using a kneader, speedmixer or a dissolver. Typically, the filler(s) is/are added to the other components. This may facilitate the mixing procedure.

The curable composition of the invention can be obtained by combining (including mixing and kneading) the individual components of the composition.

A further embodiment of the invention is directed to a kit of parts. Thus, the composition may be provided in separate parts and comprises at least a curable base paste and a catalyst or initiator paste comprising an initiator suitable for curing at least part of the material of the base paste. This can be beneficial for improving the storage stability and/or shelf life.

The individual parts of the kit can be mixed in the suitable amounts and applied using conventional techniques.

Thus, the invention also relates to a kit of parts, comprising a base paste and a catalyst paste separated from each other before use, wherein the base paste comprises the hardenable compound, the metal containing compound and the catalyst paste comprises the initiator and wherein the other optional components (e.g. filler, retarder, additive(s)) is/are present either in the base paste or the catalyst paste or in the base paste and the catalyst paste.

If a filler is present, it can be preferred, if the filler is present in the base paste only. This may be desirable from a chemical stability point of view. If the filler is present in the base paste only, the shelf life might be improved.

If the filler is present in the base paste, it is typically present in an amount of at least about 1 or at least about 5 or at least about 10 wt.-%, wt.-% with respect to the weight of the base paste. Typical ranges include from about 5 to about 70 or from about 10 to about 50 or from about 15 to about 45, with respect to the weight of the base paste.

The more equal the viscosity of the base paste compared to the catalyst paste is, and the lower the overall viscosity is, the easier the mixing can typically be achieved, especially if the mixing is done using a static mixing tip.

The volume ratios of catalyst paste and base paste can range from about 10:1 to about 1:10. Particularly preferred volume ratios of base paste to catalyst paste are from about 1:1 to about 10:1 or from about 2:1 to about 5:1 (e.g. 5 parts of base paste to 1 part of catalyst paste).

The composition is typically stored in a container until use.

If the composition is provided as a two-component or two-part system, it can be stored in a dual-chamber container or cartridge.

Cartridges which can be used are described e.g. in US 2007/0090079 (Keller et al.) or U.S. Pat. No. 5,918,772 (Keller et a.), the disclosure of which is incorporated by reference. Cartridges which can be used are also commercially available e.g. from SulzerMixpac AG (Switzerland).

Other suitable devices include those which can be found in WO 2005/016783 A1 (Reidt et al.), WO 2007/047381 (Hohmann et al.), WO 2007/104037 (Broyles et al.) and WO 2009/061884 (Boehm et al.).

If desired, the composition can also be stored in foil bags.

The disclosure of the above mentioned patents is herewith explicitly mentioned and regarded as part of the text of this invention and herewith incorporated by reference.

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1 (Keller et al.), U.S. Pat. No. 6,135,631 (Keller et al.) or EP 0 863 088 A1 (Pauser et al.) together with a dynamic mixing tip as mentioned in US 2004/0085854 (Pauser et al.) or U.S. Pat. No. 6,244,740 (Wagner et al.).

A further improvement of the handling properties of the composition can be seen in using an automatic mixing and metering systems for two-component compositions which have automatic conveying and mixing units, such as are described e.g. in U.S. Pat. No. 5,249,862 (Herold et al.), U.S. Pat. No. 5,286,105 (Herold et al.) and U.S. Pat. No. 5,419,460 (Herold et al). The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

In practice, the composition (if provided as a two-component system) can be syringed through a static or dynamic mixing device onto a surface or into an impression tray or onto the patients' teeth or tissue and placed in the patients' mouth. The mixed pastes may also be applied using an applicator like an elastomer syringe.

The composition can be cured at ambient temperature or a temperature which is typically present in the mouth of a patient (e.g. within a range from about 15 to 40° C.) at ambient pressure (e.g. within a range from about 850 to 1100 hPas).

The inventive composition can be used in the dental field or as dental material.

The composition can be used as dental impression material or for the production of crowns and/or bridges, including temporary or long term crowns and bridges. In the latter case, the composition is used as a mould to be filled with the (temporary or long term) crown and/or bridge material, which is typically based on polymerizable (meth)acrylates or similar chemical reactants.

The curable composition is especially useful for producing dental materials like precision impression materials, bite registration materials, duplicating materials, modelling materials, situation impression materials.

The composition can be used e.g. for making impressions of soft and hard dental tissue. This can be achieved simply, e.g. filling the material into a dental tray and putting the tray into the mouth of a patient.

Thus, the invention is also related to a method comprising the steps
 a) providing a composition as described in the present text,
 b) bringing the composition into contact with the surface of dental tissue,
 c) letting the composition set, d) removing the cured composition from the surface of the dental tissue.

The term "dental tissue" means hard (e.g. tooth) and soft dental tissue (e.g. gum).

If used in the dental field, curing is preferably carried out at a temperature below about 50° C. and preferably below about 40° C. A typical time for cure of curable compositions of the invention used for dental impressioning is within about 20 min, or preferably within about 10 min, after mixing the components of the composition. For dental duplicating applications or dental modelling applications that take place in the professional dental laboratory, cure times of up to 45 min is generally acceptable. In other applications (e.g., sealing, moulding, coating, adhesively fixing), other cure times may be typical and higher cure temperatures may be acceptable. Nevertheless, setting times in the range of about 30 min or about 1 hour can still be useful.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

Features and advantages of this invention are further illustrated by the following examples, which are in no way intended to be limiting thereof.

EXAMPLES

Unless otherwise indicated, all parts and percentages are on a weight basis, all water is de-ionized water and all molecular weights are weight average molecular weight. Moreover, unless otherwise indicated all experiments were conducted at ambient conditions (23° C.; 1013 mbar).

General Procedures:

Mixing was typically done using a standard laboratory mixer for about 1 h without vacuum and 15 min with vacuum.

Description of Measurements

Shore Hardness A

Shore Hardness A is a very convenient method to obtain data about the degree of vulcanization. The value of Shore Hardness is a common number in dentistry to characterize a cured impression material. Measurements were done according to DIN 53505. For determination of the values three independent measurements were performed. A "Härteprüfgerät Zwick 3150 H04" (Zwick GmbH &Co. Ulm) was used as the measuring device.

Determination of Setting Time

The setting time of the compositions was determined by measuring the tan δ (delta) value of the mixed base and catalyst paste in dependence on the time at 23° C. and 50% humidity by using a MCR 300 rheometer (plate/plate measurement system) from Anton Paar. The setting time "tE" and the working time "tA" were determined with the software supplied with the instrument using a curve analysis via tangent method. As known to the skilled person in the art, the tan δ value is the quotient of the plastic and elastomeric portion of the composition.

Preparation of Base Paste 28.0% difunctional aziridino polyether (polyether back bone is a copolymer EO/THF with a molecular weight of about 6000 g/mole), 5.0% polyether (polyether back bone is a copolymer EO/THF with a molecular weight of about 6000 g/mole), 5.0% fat (triester of glycerine), 1.0% ethylene/propylene oxide block copolymer surfactant with a molecular weight of about 2650 g/mole, 6.0% dibenzyl toluene, 1.0% retarder (imidazole containing compound), 42.7% surface modified quartz filler, 8.0% diatomaceous earth, 3.4% additives (metal oxide(s), pigments, flavours and stabilisers) were mixed.

The metal containing compounds were added to this formulation.

Preparation of Catalyst Paste 32.7% of sulfonium dodecylethyl[1-(2-methoxy-2-oxoethyl)-3-oxo-3-(pentyloxy)propyl]-, tetrafluoroborate(1-) (1:1), 22.7% ethylene/propylene oxide block copolymer surfactant with a molecular weight of about 2650 g/mole, 6.4% butyltrihexylcitrate, 3.0% polytetrahydrofuran with a molecular weight of about 650 g/mole, 22.1% pyrogenic silica, 12.0% diatomaceaous earth and 1.2% pigments were mixed.

The base and catalyst paste were mixed by hand in a weight ratio of about 1 to 0.2.

Several metal containing compounds which do not show the effect on the setting time are shown in Table 1, whereas the metal containing compounds showing improvements on the setting time (tE-tA) are shown in Table 2.

TABLE 1

| metal containing compound | tE – tA [min] | Shore A hardness after 8 min | Shore A hardness after 24 h |
|---|---|---|---|
| none | 6.2 | 16 | 52 |
| +1.4% zinc sulphide | 6.1 | 20 | 52 |
| +1.8% zinc titanate | 6.1 | 19 | 52 |
| +3.6% zinc iron oxide | 6.3 | 15 | 53 |
| +7.1% iron(II)-gluconate dihydrate | 6.4 | 22 | 52 |
| +3.6% iron(III)-citrate hydrate | 6.4 | 18 | 52 |
| +1.0% manganese(II)-oxide | 6.1 | 20 | 51 |
| +1.3% manganese(IV)-oxide | 6.1 | 23 | 53 |
| +2.4% aluminium(III)-hydroxide-acetate | 6.5 | 19 | 51 |
| +3.9% titanium(IV)-acetylacetonate | 6.1 | 21 | 53 |

TABLE 2

| metal containing compound | tE – tA [min] | Shore A hardness after 8 min | Shore A hardness after 24 h |
|---|---|---|---|
| +1.2% zinc(II) oxide | 3.5 | 30 | 60 |
| +1.5% zinc(II) hydroxide | 3.9 | 33 | 57 |
| +1.6% zinc(II) carbonate | 3.4 | 36 | 60 |
| +4.6% zinc(II) wolframate | 3.3 | 37 | 59 |
| +1.0% zinc(II) acetylacetonate | 2.0 | 37 | 60 |
| +0.5% zinc(II) acetylacetonate | 1.7 | 47 | 61 |
| +6.3% zinc(II) bis(undec-10-enoate) | 2.0 | 48 | 60 |
| +1.5% zinc(II) bis(neodecanoate) | 3.1 | 31 | 58 |
| +9.3% zinc(II) stearate | 2.1 | 43 | 59 |
| +2.4% copper(II)-sulphate | 2.9 | 50 | 63 |
| +0.3% copper(II)-2-ethylhexanoate | 1.9 | 49 | 62 |
| +0.6% copper(II)-2-ethylhexanoate | 2.1 | 46 | 60 |
| +3.8% nickel(II)-acetylacetonate | 1.6 | 49 | 62 |
| +4.1% silver(I)-carbonate | 2.5 | 43 | 62 |
| +2.0% silver(I)-carbonate | 3.0 | 36 | 62 |
| +1.5% silver(I)-carbonate | 3.6 | 33 | 60 |

In Tables 1 and 2 "%" means wt.-% with respect to the amount of the base paste.

The invention claimed is:

1. A curable composition to be prepared by mixing a base paste and a catalyst paste, wherein the base paste comprises
   (A) a hardenable compound comprising at least two aziridine moieties, and
   (B) a metal containing component containing anions and/or ligands, the metal containing component being present in an amount of about 0.1 to about 5 wt.-% with respect to the weight of the base paste, the metal being selected from Zn, Cu, Co, Ni, Ag and combinations thereof, the anions or ligands being selected from oxide, hydroxyl, (hydrogen)carbonate, (hydrogen)sulphate, (hydrogen)phosphate, sulphate, halide, lactate, benzoate, wolframate, linear or branched aliphatic carboxylic acid anions, ligands having not more than two coordinating moieties and combinations thereof, (E) filler being different from the metal containing component, wherein the catalyst paste comprising (C) a Lewis acid, the composition optionally further comprises (D) a retarder, and (F) additive(s), wherein the volume ratio of the base paste to the catalyst paste is about 2:1 to about 5:1, and wherein, the setting time tE-tA is less than 6.1 minutes when the curable composition is prepared by mixing the base paste and the catalyst paste, with tE-tA determined by measuring the tan δ (delta) value over time at 23° C. and 50% humidity.

2. The composition according to claim 1, wherein the hardenable compound comprises a backbone containing moieties selected from polyether, polyesters, polyamides, polyurethanes, silicones and combinations thereof.

3. The composition according to claim 1, wherein the aziridine moiety is of the following formula

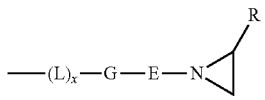

wherein

R represents H, C1-C12 alkyl, C2-C12 alkenyl, C2-C12 alkinyl, C7-C15 alkylaryl, C7-C15 arylalkyl or C3-C12 cycloalkyl, and wherein hydrogen atoms can be replaced by Cl or F and/or wherein up to about 5 carbon atoms may be replaced by atoms or group of atoms selected from O, CO, N or S, E represents a C1-C18 branched or unbranched hydrocarbon chain wherein up to about 5 carbon atoms can be replaced by atoms or group of atoms selected from O, CO, N or S, G represents a group selected from C(O)O, C(O)NR, C(O), C(O)C(O), C(O)(CH$_2$)$_m$C(O) with m=1 to 10, C(S)NR or CH$_2$, L represents O, S or NR, with x=0 or 1.

4. The composition according to claim 1, wherein the Lewis acid is selected from components comprising a sulfonium ion.

5. The composition according to claim 1, wherein the Lewis acid is of the formula

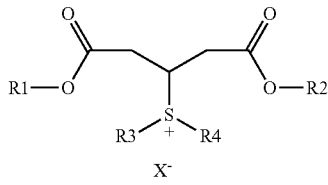

wherein X$^-$ is a non or low coordinating anion, R1, R2, R3 and R4 are independently linear, cyclic or branched C$_1$-C$_{20}$ alkyl or alkylene groups, wherein one or more of the methylene groups may be substituted by —CO—, —CONH—, —CON(CH$_3$)—, —S— and/or —O—, and wherein R1, R2, R3 and/or R4 can act as a bridging element, connecting two or more structural elements.

6. The composition according to claim 1, wherein the metal containing component is selected from zinc oxide, zinc hydroxide, zinc carbonate, zinc wolframate, zinc acetylacetonate, zinc bis(neodecanoate), zinc stearate, copper sulphate, copper 2-ethylhexanoate, nickel acetlyacetonate, silver carbonate, alone or combinations thereof.

7. The composition according to claim 1 comprising a retarder.

8. The composition according to claim 1, wherein the composition is essentially water free.

9. The composition according to claim 1 comprising one or more additive(s) selected from rheology modifier(s), thixotropic agent(s), diluting agent(s), pigment(s), dye(s), plasticizer(s), odorous substance(s), flavouring(s), stabilizer(s), surfactant(s) mixtures and combinations thereof.

10. The composition according to claim 1 comprising:
(A) hardenable compound: from about 5 to about 90 wt.-%,
(B) metal containing component: from about 0.1 to about 5 wt.-%,
(C) Lewis acid: from about 0.25 to about 50 wt.-%,
(D) retarder: from 0 to 10 wt.-%,
(E) filler: from about 1 to about 80 wt.-%, and
(F) additives: from about 0 to about 50 wt.-%,
wt.-% with respect to the weight of the whole composition.

11. The composition according to claim 1, wherein the composition characterized by at least one of the following parameters after hardening:
Elongation at break (according to DIN 53504): at least 50%,
Tensile Strength (according to DIN 53504): at least 1.0 MPa,
Shore Hardness A (according to DIN 53504; after 24 h): at least 40.

12. A kit of parts comprising a base paste and a catalyst paste, the base paste comprising a hardenable compound comprising at least two aziridine moieties, a metal containing component in an amount of about 0.1 to about 5 wt.-% and a filler, wherein the metal of the metal containing component is selected from Zn, Cu, Co, Ni, Ag and mixtures thereof, wherein the catalyst paste comprises a Lewis acid, wherein the catalyst paste is essentially free of the metal containing component, wherein the volume ratio of the base paste to the catalyst paste is about 2:1 to about 5:1, and wherein, the setting time tE-tA is less than 6.1 minutes when the curable composition is prepared by mixing the base paste and the catalyst paste, with tE-tA determined by measuring the tan δ (delta) value over time at 23 ° C. and 50% humidity.

13. An item comprising the composition as described in claim 1.

14. A method for curing a cationically curable composition, comprising mixing the components of the cationically curable composition comprising a base paste and a catalyst paste, wherein the base paste comprises a metal containing component containing anions and/or ligands and a filler being different from the metal containing component, the metal containing component being present in an amount of about 0.1 to about 5 wt.-% with respect to the weight of the base paste, the metal being selected from Zn, Cu, Co, Ni, Ag and combinations thereof, the anions or ligands being selected from oxide, hydroxyl, (hydrogen)carbonate, (hydrogen)sulphate, (hydrogen) phosphate, sulphate, halide, lactate, benzoate, wolframate, linear or branched aliphatic carboxylic acid anions, ligands having not more than two coordinating moieties and combinations thereof, wherein the volume ratio of the base paste to the catalyst paste is about 2:1 to about 5:1, and wherein, the setting time tE-tA is less than 6.1 minutes when the curable composition is prepared by mixing the base paste and the catalyst paste, with tE-tA determined by measuring the tan δ (delta) value over time at 23° C. and 50% humidity.

15. Method of taking a dental impression comprising the steps of
 a) applying the curable composition as described in claim 1 to the surface of dental tissue,
 b) letting the curable composition set,
 c) removing the set composition from the dental tissue.

16. The composition according to claim 7, wherein the retarder comprises an imidazole moiety.

17. The item according to claim 13, wherein the item is selected from a dental impression material, a crown, and a bridge.

18. A curable composition to be prepared by mixing a base paste and a catalyst paste, wherein the base paste comprises
 (A) a hardenable compound comprising at least two aziridine moieties, and
 (B) a metal containing component containing anions and/or ligands,
  the metal containing component being present in an amount of about 0.1 to about 10 wt.-% with respect to the weight of the base paste,
  the metal being selected from Zn, Cu, Co, Ni, Ag and combinations thereof,
  the anions or ligands being selected from oxide, hydroxyl, (hydrogen)carbonate, (hydrogen)sulphate, (hydrogen)phosphate, sulphate, halide, lactate, benzoate, wolframate, linear or branched aliphatic carboxylic acid anions, ligands having not more than two coordinating moieties and combinations thereof,
 (E) filler being different from the metal containing component,
 wherein the metal containing component is only present in the base paste and the catalyst paste comprising (C) a Lewis acid, the composition optionally further comprises (D) a retarder, and (F) additive(s),
 wherein the volume ratio of the base paste to the catalyst paste is about 2:1 to about 5:1, and
 wherein, the setting time tE-tA is less than 6.1 minutes when the curable composition is prepared by mixing the base paste and the catalyst paste, with tE-tA determined by measuring the tan δ (delta) value over time at 23° C. and 50% humidity.

19. The composition according to claim 1, wherein the setting time tE-tA is 3.9 minutes or less.

20. The kit according to claim 12, wherein the setting time tE-tA is 3.9 minutes or less.

21. The method according to claim 14, wherein the setting time tE-tA is 3.9 minutes or less.

22. The composition according to claim 18, wherein the setting time tE-tA is 3.9 minutes or less.

* * * * *